March 28, 1972 H. B. LEWIS ET AL Plant Pat. 3,089
AZALEA PLANT
Filed Nov. 10, 1969
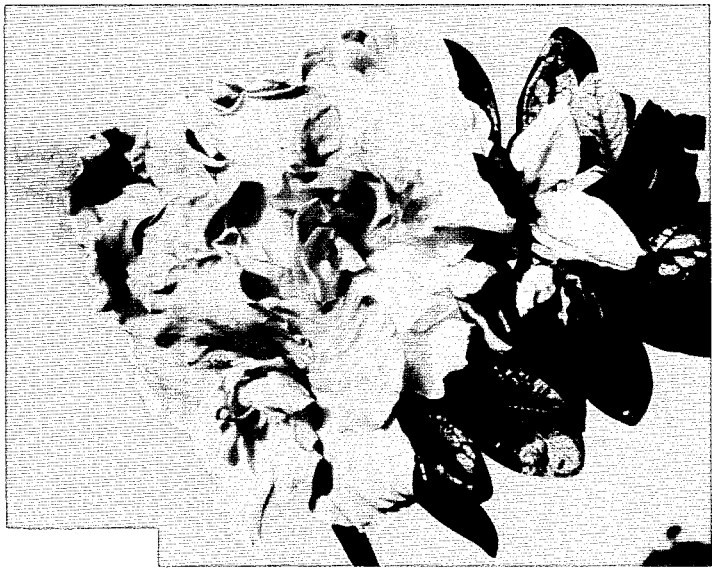
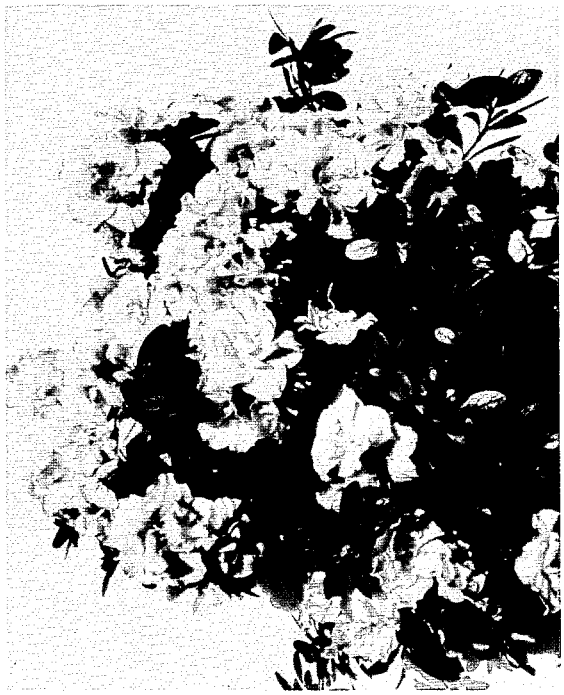
Inventors.
H. B. Lewis
H. H. Lewis
By: Robb & Robb
Attorneys.

United States Patent Office

Plant Pat. 3,089
Patented Mar. 28, 1972

3,089

AZALEA PLANT

Hubert B. Lewis and Helen H. Lewis, both of 761 Country Hill Drive, La Habra, Calif. 90631

Filed Nov. 10, 1969, Ser. No. 875,600
Int. Cl. A01h *5/00*
U.S. Cl. Plt.—56 1 Claim

The present invention relates to a new and distinct variety of azalea plant which was originated by us by crossing the azalea variety known as "Pink Pearl" (unpatented) with the azalea variety known as "Pink Perfection" (unpatented), the former being the seed parent, and the latter being the pollen parent.

As the result of this breeding, we have produced a new and improved azalea variety which is distinguished from its parents, as well as from all other azalea varieties of which we are aware, as evidenced by the following unique combination of characteristics which are outstanding in the new variety:

(1) An attractive plant form;
(2) An unusually large flower size for azalea flowers of the pink color class;
(3) A distinctive and attractive pink flower color;
(4) Good keeping qualities of the flowers, particularly when precooled, and flowers hold well under refrigeration; and
(5) Excellent suitability for greenhouse forcing.

Asexual reproduction of our new variety by cuttings, as performed by us at Whittier, Calif., shows that the foregoing characteristics and distinctions come true to form and are established and transmitted through succeeding propagations.

The accompanying drawing shows a typical specimen plant of our new azalea variety, as well as typical specimens of the flowers and foliage on a somewhat enlarged scale, all as depicted in color as nearly true as it is reasonably possible to make the same in a color illustration of this character.

The following is a detailed description of our new variety, with color terminology in accordance with the Horticultural Colour Chart issued by Wilson Colour Ltd. in collaboration with The Royal Horticultural Society, except where general color terms of ordinary dictionary significance are obvious:

Breeding: Seedling.
*Seed parent.*—"Pink Pearl."
*Pollen parent.*—"Pink Perfection."
Propagation: Holds its distinguishing characteristics through succeeding propagations by cuttings.
Locality where grown and observed: Whittier, Calif.

*Plant*

Form: Bush; much-branched.
Habit: Vigorous branching and sprawly; needs pruning to shape.
Rooting: Good.
Blooming habit: Heavy bloomer.
Blooming season: All year around under appropriate culture conditions; very good suitability for forcing.

Foliage:
*Size.*—Medium.
*Quantity.*—Abundant.
*Color.*—New foliage: Upper side—Spinach Green, Plate 0960, page 187. Under side—Lettuce Green, Plate 061/1, page 176. Old foliage: Upper side—Parsley Green, Plate 00962, page 193. Under side—Spinach Green, Plate 0960/2, page 187.
*Shape.*—Oval pointed.
*Texture.*—Upper side—glossy. Under side—rough.
*Margin.*—Smooth edge.
*Aspect.*—Good.
*Disease resistance.*—Quite free of diseases to which azalea plants are normally subject, as determined by comparison with other varieties grown under the same cultural conditions at Whittier, Calif.

*Flowers*

Borne: 2 or 3 to stem; on short stems.
Quantity of bloom: Free, both outdoors and in greenhouse.
Continuity: Intermittent.
Permanence: From 2 to 3 weeks.
Size: Very large for pink class; about 4 inches in diameter.
Petalage:
*Number of petals under normal conditions.*—5.
*Texture.*—Firm.
*Color.*—Upper portion—Fuchsine Pink, Plate 627/3, page 78. Lower portion—Fuchsine Pink, Plate 627/2, page 78, in form of irregular dots in throat.
*Appearance.*—Inside—good pink color. Outside—good pink color.
*Shape.*—From single to semi-double.
*Arrangement.*—Single, with 5 petals joined at base, and with single to tufted center.
Bud:
*Color.*—Fuchsine Pink, Plate 627/2, page 78.

*Reproductive organs*

Stamens:
*Color.*—Fuchsine Pink, Plate 627/3, page 78.
Pollen:
*Color.*— Yellow
Styles:
*Color.*—White.
Ovaries:
*Color.*—Green.

We claim:

1. A new and distinct variety of azalea plant, substantially as herein shown and described, characterized particularly as to novelty by the unique combination of an attractive plant form, an usually large flower size for azalea flowers of the pink color class, a distinctive and attractive pink flower color, good keeping qualities of the flowers, particularly when pre-cooled, and flowers hold well under refrigeration, and excellent suitability for greenhouse forcing.

No references cited.

ROBERT E. BAGWILL, Primary Examiner